(12) United States Patent
Inouye et al.

(10) Patent No.: US 11,723,770 B2
(45) Date of Patent: Aug. 15, 2023

(54) STRAIN-RELIEVING SLEEVE FOR CARDIOVASCULAR DEVICES

(71) Applicant: Boston Scientific Scimed, Inc., Maple Grove, MN (US)

(72) Inventors: Joshua M. Inouye, Maple Grove, MN (US); James M. Anderson, Corcoran, MN (US); John M. Edgell, Plymouth, MN (US); Graham Krumpelmann, Stillwater, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 284 days.

(21) Appl. No.: 16/923,461

(22) Filed: Jul. 8, 2020

(65) Prior Publication Data

US 2021/0007846 A1   Jan. 14, 2021

Related U.S. Application Data

(60) Provisional application No. 62/871,791, filed on Jul. 9, 2019.

(51) Int. Cl.
  *A61F 2/24* (2006.01)

(52) U.S. Cl.
  CPC .......... *A61F 2/2445* (2013.01); *A61F 2/2466* (2013.01); *A61F 2210/0014* (2013.01)

(58) Field of Classification Search
  CPC ............................ A61F 2/2445; A61F 2/2466
  See application file for complete search history.

(56) References Cited

U.S. PATENT DOCUMENTS

| | | | |
|---|---|---|---|
| 9,610,156 | B2 | 4/2017 | Lashinski |
| 9,615,926 | B2 | 4/2017 | Lashinski et al. |
| 9,622,862 | B2 | 4/2017 | Lashinski et al. |
| 9,848,983 | B2 | 12/2017 | Lashinski et al. |
| 10,335,275 | B2 | 7/2019 | Lashinski et al. |
| 10,548,731 | B2 | 2/2020 | Lashinski et al. |
| 10,555,813 | B2 | 2/2020 | Lashinski et al. |
| 2018/0228610 | A1* | 8/2018 | Lashinski ............. A61F 2/2466 |

* cited by examiner

*Primary Examiner* — William H Matthews
(74) *Attorney, Agent, or Firm* — Seager, Tufte & Wickhem, LLP

(57) ABSTRACT

An actuator sleeve includes resiliency features that may reduce chronic strain on valve annulus implants. The resiliency features may relate to one or more of a material, a manufacture, a dimension, and/or design attribute of the sleeve. In one aspect the resiliency features may allow deformation of the sleeve at frame interfaces to distribute forces to reduce the frame fatigue.

20 Claims, 9 Drawing Sheets

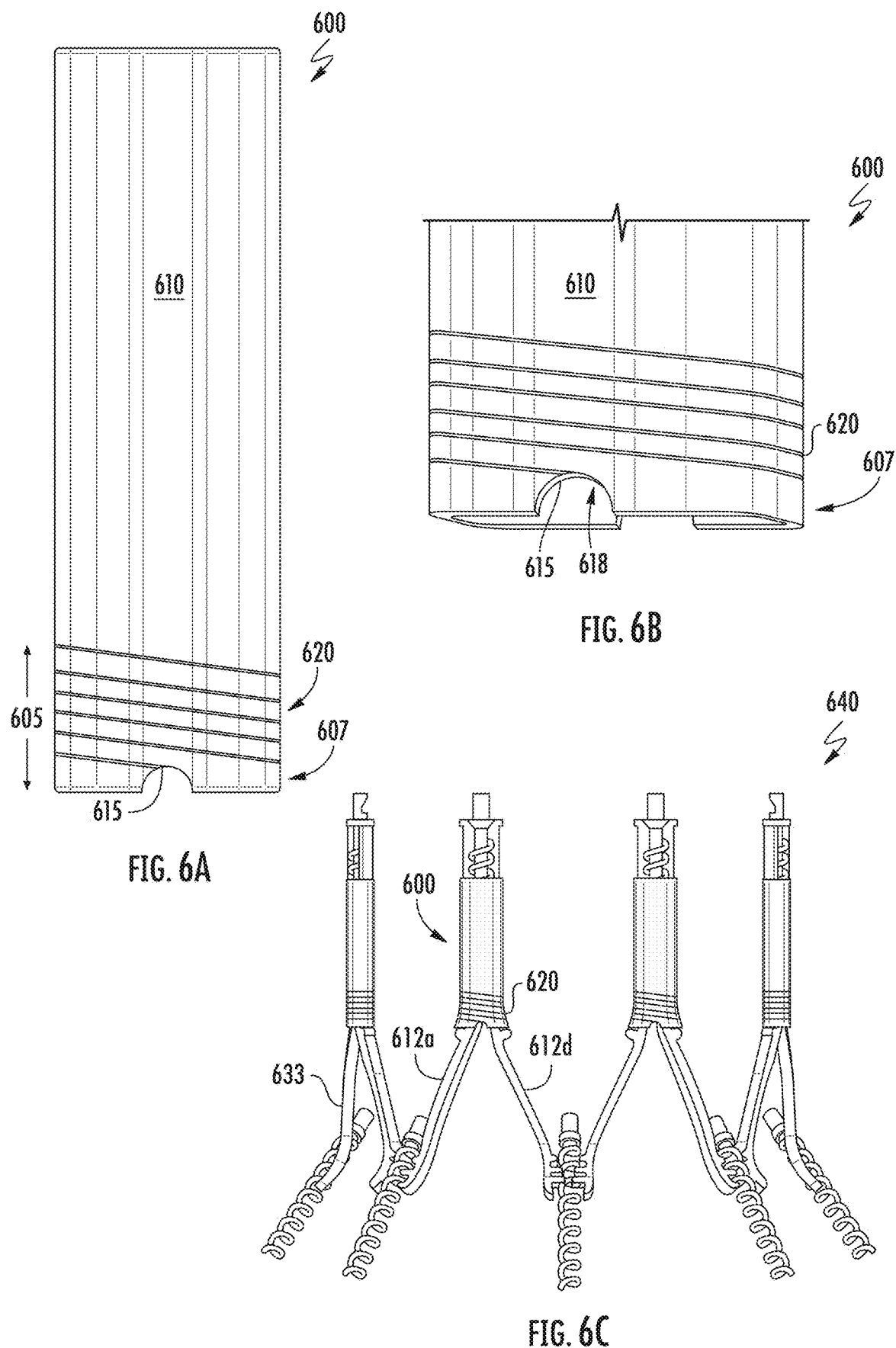

STRAIN-RELIEVING SLEEVE FOR CARDIOVASCULAR DEVICES

CROSS-REFERENCE TO RELATED APPLICATION

The present application claims the benefit of priority under 35 U.S.C. § 119 to U.S. Provisional Patent Application 62/871,791, filed Jul. 9, 2019, which application is incorporated herein by reference in its entirety for all purposes.

FIELD

The present disclosure relates generally to the field of implantable medical devices and more particularly to implantable devices, systems, and methods for adjusting heart features.

BACKGROUND

The mitral valve lies between the left atrium and the left ventricle of the heart. The mitral valve includes an anterior leaflet and a posterior leaflet that coapt during systolic contraction. The mitral annulus is a saddle shaped fibrous ring that surrounds the mitral valve and supports the valve's leaflets. Mitral insufficiency (MI) is a form of heart disease where the mitral annulus excessively dilates and the valve leaflets no longer effectively coapt during systolic contraction. Regurgitation occurs during ventricular contraction and cardiac output decreases.

Annuloplasty is performed to regain mitral valve competence by restoring the physiological form and function of the normal mitral valve. Annuloplasty procedures may involve implanting a structure, such as a ring, stent, frame, or the like within the heart. Cardiac implants are subject to the chronic stresses and strains associated with cardiac muscle palpitation and it would thus be desirable to reduce the impact of chronic forces on a cardiac implant.

SUMMARY

Embodiments of the present disclosure relate to a valve annulus implant comprising resilient components configured to reduce the effects of chronic forces upon the implant during use. According to one aspect, an implant includes a frame having a proximal end, a distal end, and adjacent struts joined at an apex. The implant may also include a sleeve disposed about the apex, the sleeve configured to apply a force to the frame at one or more contact points, the sleeve including a resiliency feature selected to reduce stress resulting from the force at the one or more contact points. The resiliency feature may include one of a sleeve material and/or a sleeve design. The sleeve material may include one or more of nitinol, stainless steel, a polymer and cobalt chrome or other similar material. In some embodiments, the sleeve material may vary in elasticity and/or resilience at different locations of the sleeve. In addition, the sleeve may comprise a sleeve body having a bore extending therethrough, and the sleeve material is a hybrid material including a first material disposed within the bore and a second material disposed at least partially around the bore. The second material may be less elastic than the first material. The first material may coat at least a portion of the bore proximate to at least one contact point. The first material may alternatively comprise a bumper that is fixedly attached to the bore proximate to at least one contact point. In addition, or alternatively the sleeve design may include one or more sleeve slots. The sleeve slot may extend proximally from a distal end of the sleeve for a slot extent. The sleeve slot may differ in width over the slot extent. The sleeve slot may be greater than half a width of the sleeve. In addition, or alternatively, the sleeve slot may extend longitudinally along the sleeve or helically around the sleeve for the slot extent. The sleeve slot may extend helically around the sleeve for one or more turns. The sleeve slot may vary in pitch over the one or more turns. In addition, the implant may comprise a plurality of sleeve slots. At least two of the plurality of sleeve slots may be disposed on opposing sides of the sleeve or the same side of the sleeve. At least two of the plurality of sleeve slots may comprise different slot extents.

According to another aspect, an implant delivery system includes a delivery catheter and a frame having a compressed configuration for advancement through the delivery catheter to a valve annulus and an expanded configuration for placement of the frame proximate the valve annulus for repair. The frame may include a proximal end, a distal end, and adjacent struts joined at an apex, and an actuator comprising a sleeve disposed about the apex, the actuator configured to drive the sleeve over the apex by pushing or rotating the actuator to compress the frame to a cinched configuration in which a force is applied to the adjacent struts to adjust a space between the adjacent struts. The sleeve may include a resiliency feature including one or both of a sleeve composition or a sleeve design configured to reduce the force exerted by the sleeve on the frame.

According to a further aspect, a method for deploying an implant for reshaping a valve annulus at a valve annulus site includes the step of deploying an implant to a valve annulus site, the implant comprising a frame including a pair of struts joined at an apex and an actuator comprising a sleeve disposed about the apex. The method includes driving the actuator to drive the sleeve down the apex by pushing or rotating the actuator to compress the frame to a cinched configuration in which a force is applied to the adjacent struts to adjust a space between the adjacent struts, wherein driving the actuator may cause the sleeve to at least partially deform to reduce the force exerted by the sleeve on the frame.

With such an arrangement, the resilient features may reduce the fracture risks by diminishing the impact of chronic stress and strain on the frame.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical illustrated component is typically represented by a single numeral. For purposes of clarity, not every component is labeled in every figure, nor is every component of each embodiment shown where illustration is not necessary to allow those of ordinary skill in the art to understand the disclosure. In the figures:

FIGS. 6A-6C illustrate perspective views of an embodiment of a resilient sleeve in accordance with the present disclosure;

DETAILED DESCRIPTION

Annuloplasty implants may include components that interact and may experience fatigue during chronic operation of the implant. According to one aspect, an improved annuloplasty implant includes one or more resilient components configured to reduce the deleterious effects of component interaction. In one embodiment, an actuator sleeve of a cinching implant may be configured with at least one resiliency feature to improve the ability of the actuator sleeve to absorb the stress and strains caused by actuator sleeve/frame interaction. In various embodiments, the resiliency feature may relate to one or more of a material, a manufacture, a dimension, and/or design attribute of the actuator sleeve. In some embodiments, the resiliency feature may increase the elasticity of the actuator sleeve at contact points to absorb stress. Alternatively, or in conjunction, the resiliency feature may increase a deformability of the actuator sleeve, thereby increasing a contact surface area to better distribute stress along the sleeve.

These and other beneficial aspects of a resilient sleeve and method of manufacture and/or use are described in more detail below. It should be noted that, although embodiments of the present disclosure may be described with specific reference to mitral valves, the principles disclosed herein may be readily adapted to facilitate reconstruction of any valve annulus, for example including a tricuspid valve annulus and/or may similarly benefit any other dilatation, valve incompetency, valve leakage, and other similar heart failure conditions.

As used herein, the term "distal" refers to the end farthest away from the medical professional when introducing a medical device into a patient, while the term "proximal" refers to the end closest to the medical professional when introducing a medical device into a patient.

Figure 1A:
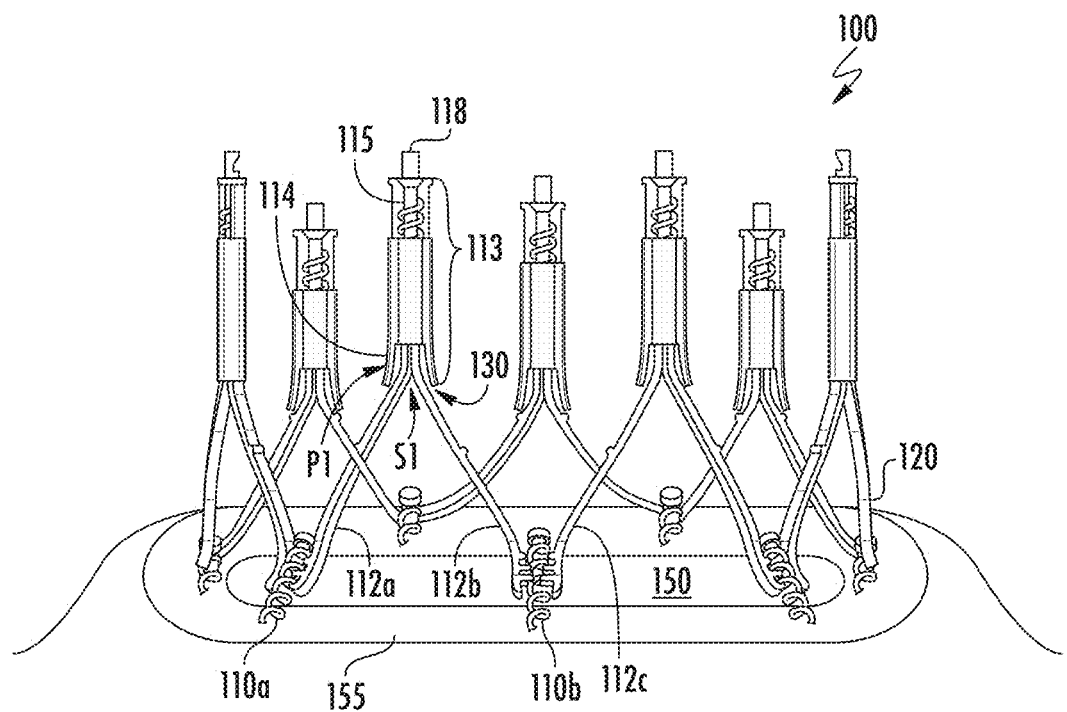
FIG. 1A illustrates an implant including a resilient actuator sleeve in accordance with one embodiment of the present disclosure.

FIG. 1A illustrates an implant 100 comprising a frame 120 disposed about a valve 150. The frame 120 of the implant 100 supports actuators 113 and anchors 110a, 110b, wherein for purposes of clarity not all of the components of the implant are numbered. In one embodiment, the frame 120 may extend circumferentially around and partially axially along a central frame axis extending proximally-distally through a center point of the frame such that anchors 110a, 110b disposed on a distal end of the frame 120 are positioned proximate to a valve annulus 155. The frame 120 may be generally symmetric with respect to the central frame axis although it need not be symmetric. The frame 120 may form a generally tubular shape, where herein "tubular" includes circular as well as other rounded or otherwise closed shapes. The frame 120 may be configured to change shape, size, and/or configuration. For example, the frame 120 may assume various shapes, sizes, configurations etc. during different phases of deployment such as during pre-delivery, delivery, tissue engagement, and cinching.

According to one embodiment, the frame 120 may be formed from one or more struts 112a, 112b, and 112c that may form all or part of the frame 120, where the struts 112a, 112b, and 112c may include elongated structural members formed of a metal alloy, a shape memory material, such as an alloy of nickel titanium or other metals, metal alloys, plastics, polymers, composites, other suitable materials, or combinations thereof. In FIG. 1A, fourteen struts are shown although it is appreciated that in some embodiments, there may be fewer or more than fourteen struts.

In one embodiment, the struts of the frame 120 may be formed from the same, monolithic piece of material (e.g. tube stock). Thus, reference to struts 112a, 112b, and 112c may refer to different portions of the same, extensive component. Alternatively, reference to struts 112a, 112b, and 112c may refer to components that are formed separately and attached permanently together, for example by welding or other methods. In some embodiments, the struts 112a, 112b, and 112c may be separate components that are detachably coupled together to form proximal and distal apices. For example, the struts 112a, 112b are shown joined at their proximal ends to form a proximal apex with an actuator 113 mounted thereto. Struts 112b and 112c are joined at their distal ends with an anchor 110b coupled thereto.

Figure 1B:
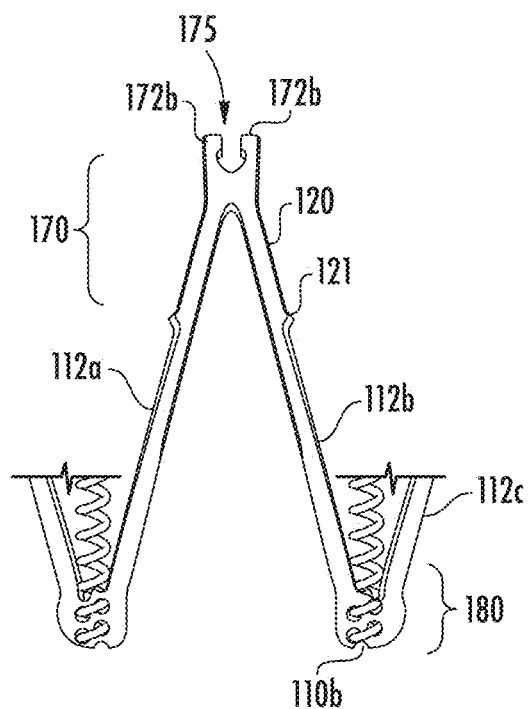
FIG. 1B illustrates a portion of a frame of the implant of FIG. 1A.

In some embodiments, the terms "apex," apices," and the like may be used interchangeably with terms "crown," "crowns," and the like, as used herein and as used in any reference incorporated by reference herein, unless otherwise stated. In one embodiment, an 'apex' may include a proximal or distal portion of the frame. For example, FIG. 1B illustrates a portion of the frame 120, where actuators have been removed to expose the proximal apex 170 of the frame 120. A proximal apex 170 may include the portion of the frame where struts 112a, 112b adjoin, and a distal apex 180 may include the portion of the frame where struts 112b and 112c adjoin. The apex may also include that portion of the frame that may be constrained by the structure that adjoins the struts to form the apex. For example, a distal apex 180 includes the portion of the struts 112b, 112c having openings supporting anchor 110b. Proximal apex 170 includes the portion of struts 112a, 112b configured to support an actuator (not shown), and including the portion of the struts 112a, 112b along which the actuator may travel. In the embodiment of FIG. 1B, each strut is shown to include a flange, such as flange 121 configured to limit the extent of distal travel of the actuator, and thus the proximal apex 170 includes the portion of the strut extending from the flange 121 to the proximal tips 172a, 172b of the struts 112a, 112b. In the embodiment of FIG. 1B, the proximal apex 170 of the frame 120 is arranged to form a window 175 which is configured to carry a head of an actuator shaft. Other embodiments, wherein the frame is oriented such that anchors are more proximally located than sleeves such that a distal apex carries the sleeves and a proximal apex carries the anchors are also within the scope of this disclosure.

Referring back to FIG. 1A, in one embodiment, the actuator 113 includes an actuator shaft 115 that is rotatably carried by the proximal end of the frame 120, for example, the head of the actuator shaft 115 may be carried by the window 175 (FIG. 1B) of the proximal apex 170 of the frame 120. The sleeve 114 may include internal features configured to interact with the features of the actuator shaft 115, such that rotation of the actuator shaft 115 by a drive shaft (not shown) coupled to drive coupler 118 axially translates the sleeve 114 over the actuator shaft 115 and over struts 112a, 112b. In some embodiments, "axial" as applied to axial movement or restraint of the sleeves includes directions that are at least partially in the proximal or distal direction and that are parallel or generally parallel to a central axis extending through (e.g. proximally—distally) the frame. As shown in FIG. 1A, struts 112a and 112b extend away from the proximal apex in opposing directions. Distal advancement of the sleeve 114 over struts 112a, 112b pulls the struts together within the sleeve, and as a result reduces the distance between anchors 110a, 110b to reshape an annulus 155 around the valve 150. In one embodiment, each sleeve 114 may be independently actuated in accordance with the reshaping objective for the associated anchor pair. When each sleeve has been actuated to configure their associated anchor pair, the drive shafts (not shown), coupled to drive couplers 118 may be released from the implant.

According to one aspect, each sleeve 114 may include one or more resiliency features configured to reduce the impact of chronic contact between the sleeve 114 and struts 112a, 112b. Such resiliency features may reduce the pressure of sleeve 114 upon the strut at edge contact points, such as at pressure point P1 of strut 112a, when the sleeve 114 is distally translated over strut 112a. Absent such resiliency features, the pressure P1 results in stress at stress point 51 of strut 112a, potentially causing fatigue of frame 120 over time. Resiliency features may increase the elasticity and/or deformability of the sleeve 114, to reduce the impact of pressure P1 and associated stress 51. For example, in FIG. 1A, sleeve 114 is shown to include a sleeve window 130, that enables the sleeve 114 to deform at its distal end to relieve stresses applied by the sleeve 114 on the struts 112a, 112b.

Figures 2A, 2B:
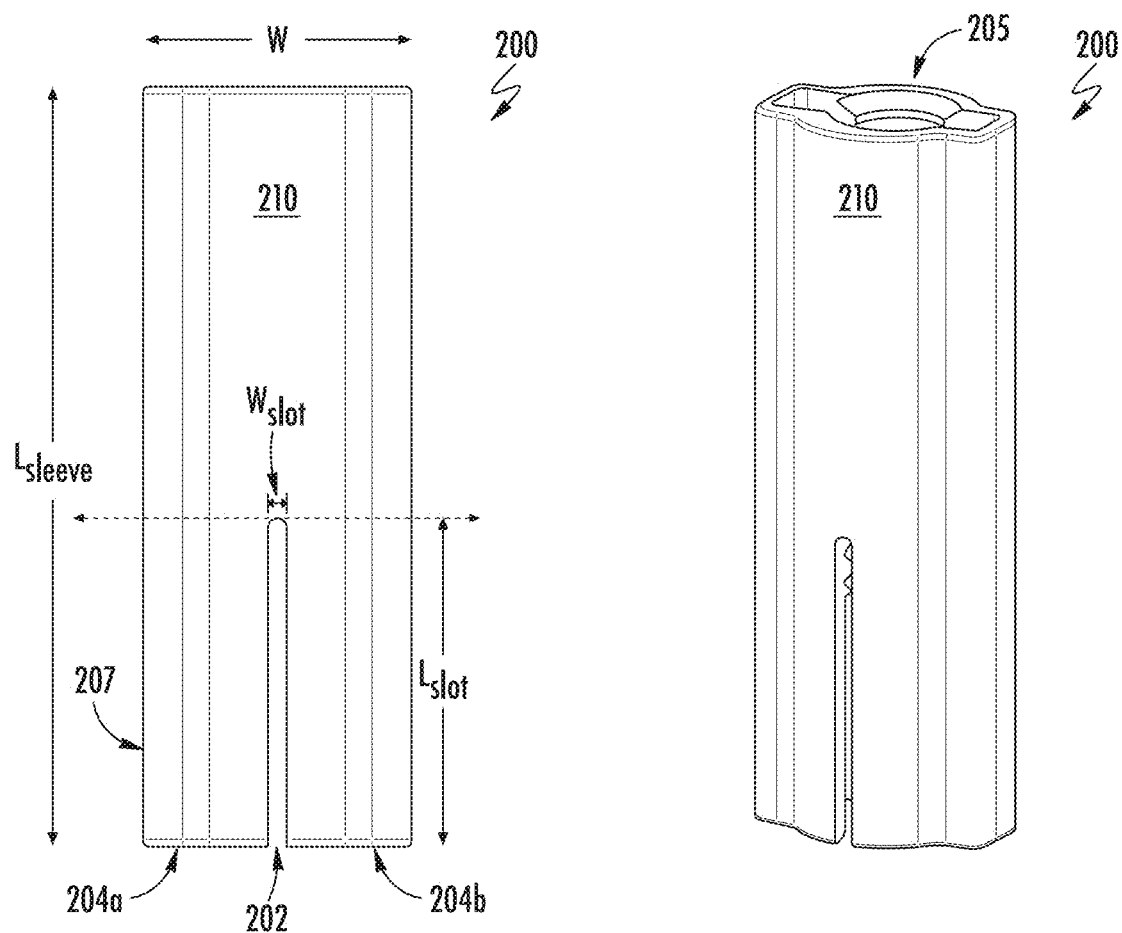
FIG. 2A is an elevational view and 2B is a perspective view of an embodiment of a resilient sleeve in accordance with the present disclosure.

FIGS. 2A-2B illustrate views of one embodiment of a resilient sleeve 200, which is similar to sleeve 114 of FIG. 1A. Sleeve 200 is shown to include a unitary body 210 having a bore 205 extending therethrough configured for rotary actuation of the sleeve 200. The bore 205 may include a threaded internal surface that interacts with threads of a shaft supported by an apex of the frame (not shown) to translate a distal end 207 of the sleeve 200 over struts of a frame as described with regard to FIG. 1A.

In some embodiments an example of a sleeve may have a length $L_{SLEEVE}$ (Height) of 0.300" and width $W_{SLEEVE}$ of 0.100" although it is appreciated that the length and width of the sleeve are a matter of design and relate to an architecture of the frame.

According to one aspect, the actuator sleeve may include a resiliency feature such as sleeve slot 202 configured to distribute contact point stress more effectively along the implant. For example, the resiliency feature may be configured to increase the contact surface area between the sleeve 200 and struts 112a, 112b (FIG. 1) by enabling the sleeve 114 to more effectively deform over the struts.

Sleeve slot 202 may extend partially or fully through the body 210 of the sleeve into the bore 205. Alternatively, a sleeve slot may extend internally from the bore through or partially through the body 210 to a sleeve surface. The sleeve slot 202 comprises a length $L_{SLOT}$ and a width $W_{SLOT}$. In FIG. 2A, the sleeve slot 202 apportions at least a front face of sleeve 200 into two legs 204a, 204b. In various embodiments, the length $L_{SLOT}$ of the sleeve slot 202 may extend from between 5%-55%, or 50%-75% of a length $L_{SLEEVE}$ of the sleeve 200. In some embodiments, the length $L_{SLOT}$ may extend along all or a portion of the sleeve 200 that covers the proximal apex of the frame when the sleeve 200 is translated to a distal-most extent, for example where a distal end 207 of sleeve 200 contacts a flange 121 (FIG. 1B) of the frame. In an exemplary embodiment, where the length $L_{SLEEVE}$ of a sleeve 200 is 6-12 mm, and the sleeve 200 is configured to travel 3-8 mm over the proximal apex of the frame, the length $L_{SLOT}$ may range between 1-4 mm and the width $W_{SLOT}$ may range between 0.25-2 mm. Although the sleeve slot 202 is shown to be generally rectangular, there is no limit to the shape of the slot 202, and, for example, slot shapes that are sinusoidal, zig-zag, dashed, angular, repetitive, semi-repetitive, etc. are also encompassed by the present disclosure. Although in FIG. 2A and FIG. 2B the sleeve slot 202 is shown to extend through the distal end 207 of the sleeve 200, it is not a requirement. Rather, it is appreciated that embodiments of a sleeve 200 in which a sleeve slot 202 does not extend through a distal end of the sleeve may include fewer sharp edges.

The width $W_{SLOT}$ of the sleeve slot 202 may be selected based on one or more considerations including, but not limited to, the width of the struts, the spacing between struts, the form of actuation (which may relate to features within the bore 205), the material of the frame, the material of the sleeve, etc. In some embodiments, the width $W_{SLOT}$ may vary over the length $L_{SLOT}$, for example to form a triangular shape, a semi-circular shape, diamond shape, or other cut-out type pattern. According to one aspect, the sleeve slot 202 may impart a resiliency to the sleeve 200, enabling a degree of expansion and contraction of the sleeve to dampen and/or distribute the forces applied to the frame by the sleeve to mitigate against fracture risk.

It is recognized that the exact form (in terms of length, width, etc.) of a resiliency feature may vary in accordance with design considerations such as frame material, sleeve material, actuation type, frame design, implant location, etc. In general, the resiliency feature is selected to allow the sleeve to perform its intended function of engaging and retaining the frame while reducing the chronic impact of such engagement.

Figure 3A:
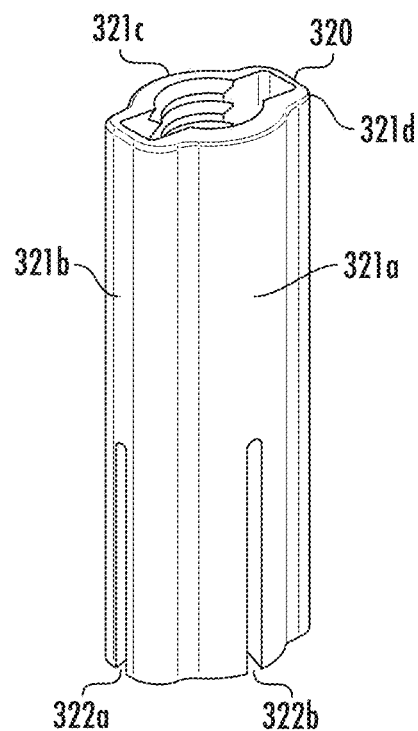
FIGS. 3A and 3B are perspective views of an embodiment of a resilient sleeve in accordance with the present disclosure.
Figure 3B:
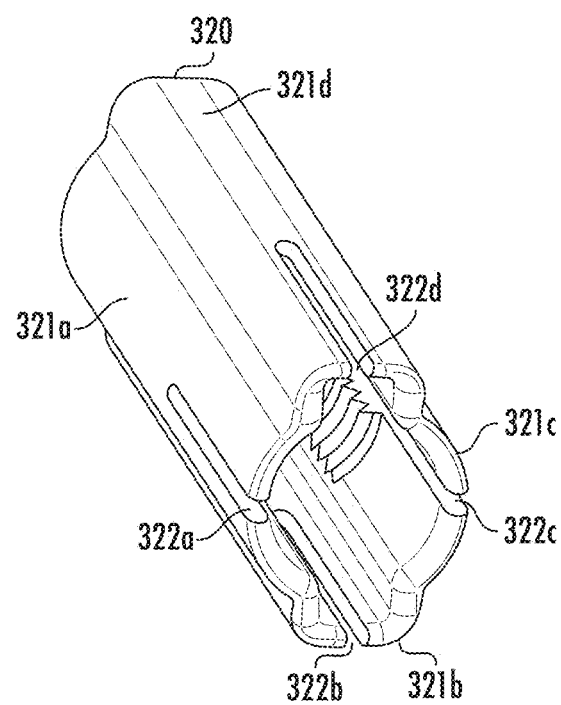

According to one aspect, a sleeve 200 is not limited to a single resiliency feature but may incorporate multiple similar or different resiliency features. For example, FIGS. 3A and 3B illustrate perspective views of a sleeve 320 having multiple sleeve slots 322a, 322b, 322c, and 322d, each sleeve slot disposed on a different surface 321a, 321b, 321c, and 321d of the sleeve 320. Although four sleeve slots 322a-322d are shown, it is appreciated that resiliency features may be disposed upon any portion or surface of a sleeve that experiences chronic contact with the frame. In some embodiments, it may be advantageous to provide slots on opposing surfaces of the sleeve, such as sleeve slot 322a on sleeve surface 321a, and slot 322c on surface 321c. Although the slots 322a, 322b, 322c, and 322d are shown as substantially similar in FIGS. 2A and 2B, it is appreciated that the particular resiliency feature selected may vary based upon the form of contact between the frame and the sleeve at the particular position. For example, in some embodiments sleeve slots 322b and 322d on the sides of the sleeve 320 may be shorter than sleeve slots 322a and 322c to retain sleeve integrity and cinching ability of the side faces 321b and 321d, while relatively longer slots 322a, 322c would enable deformity of the sleeve 320.

Figure 4:
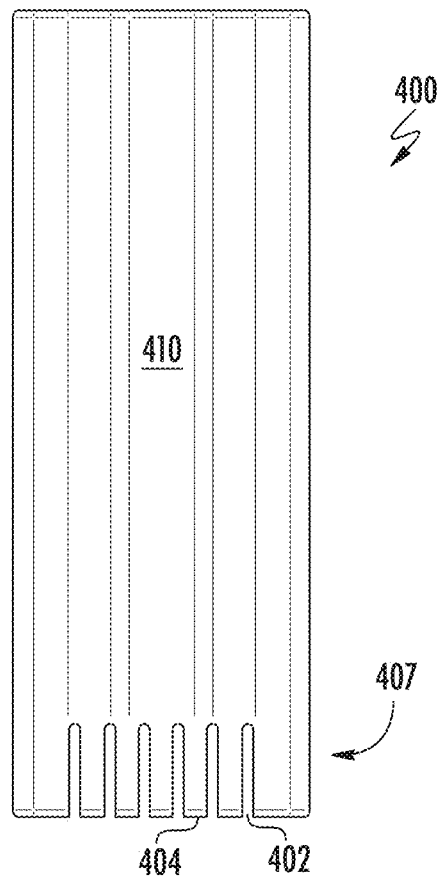
FIG. 4 illustrates an embodiment of a resilient sleeve in accordance with the present disclosure.

FIG. 4 illustrates an embodiment of a sleeve 400 including a plurality of sleeve slots, such as sleeve slot 402, extending through a surface 410 of the sleeve. The sleeve slots 402 apportion the distal end 407 of the sleeve 400 into a plurality of tabs, such as tab 404. Although the sleeve slots 402 are shown of uniform length, it is not a requirement, and it is appreciated that in some embodiments the lengths of the slots 402 may vary, for example tapering from longer slots disposed on a central portion of the surface 410, with a slot length tapering to shorter slots along the edges of the sleeve or visa-versa. Although only one surface is shown in FIG. 4, it is appreciated that a similar or different pattern of slots may be provided on other surfaces of the sleeve 400. In addition, although the width and spacing of slots 402 is shown to be relatively uniform, in various embodiments the width and spacing of slots 402 may vary, resulting in tabs 404 having different widths to provide different degrees of deformity therebetween.

Figure 5A:
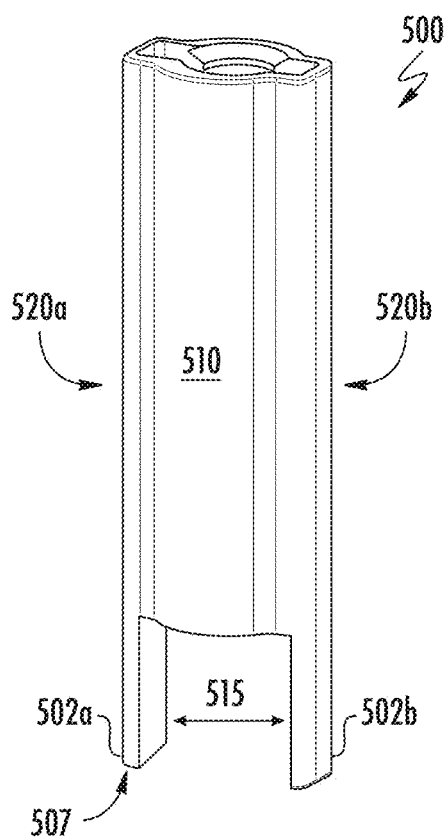
FIGS. 5A-5C illustrate perspective views of an embodiment of a resilient sleeve in accordance with the present disclosure.
Figure 5B:
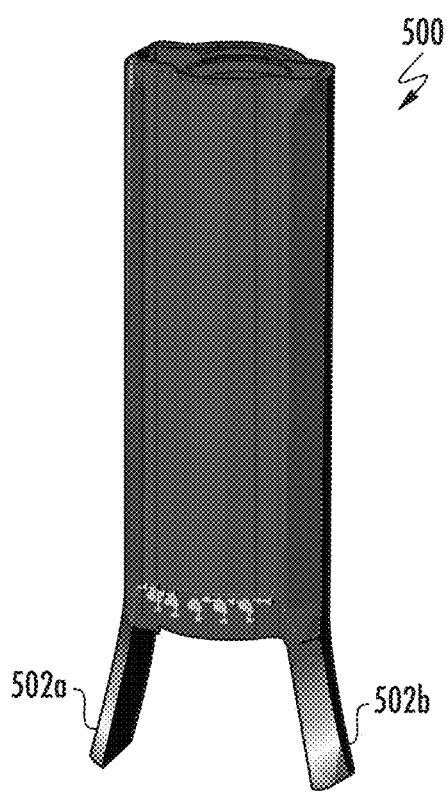
Figure 5C:
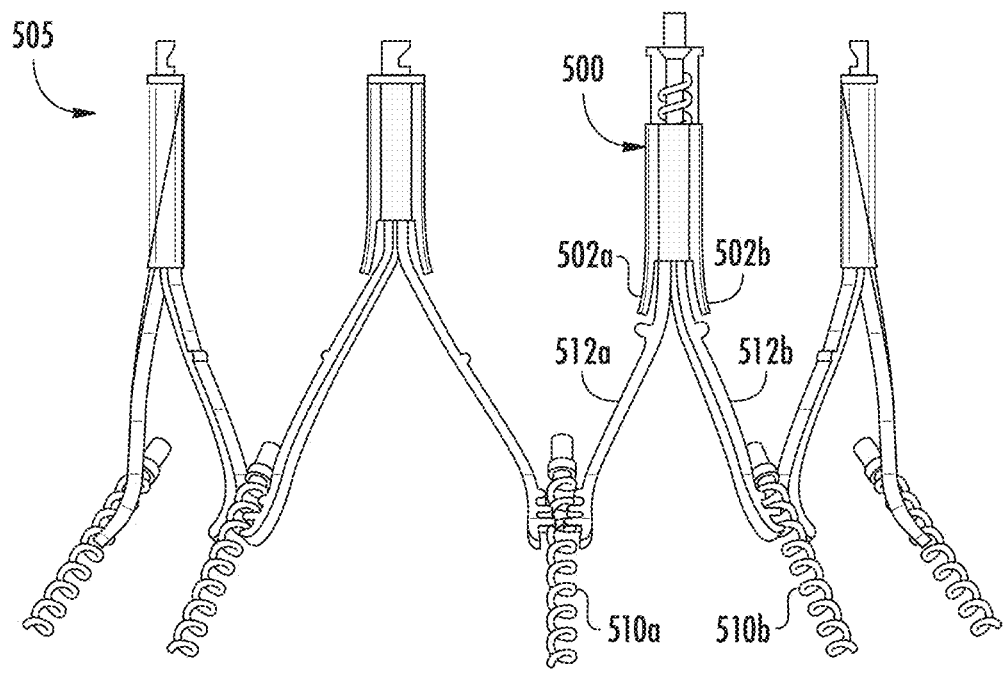

FIGS. 5A-5C illustrate another embodiment of a resilient sleeve 500. In FIG. 5A, a front surface 510 and two side surfaces 520a, 520b of the sleeve 500 can be seen. According to one aspect, the resiliency feature of sleeve 500 includes a window 515 cut through the front surface and/or rear surface of the sleeve 500, the window defining a pair of arms 502a, 502b that extend along the side surfaces 520a, 520b of the sleeve 500 to its distal end 507. In essence, the window 515 is a wide slot that extends across or partially across the front surface 510 and/or rear surface (not shown) of the sleeve. According to one aspect, the arms 502a, 502b of sleeve 500 absorb the pressure exerted by the sleeve 500 on the frame during use.

For example, FIG. 5B is a 'heat map' of the sleeve 500 intended to illustrate the strain experienced by the arms 502a, 502b of the sleeve 500 when the arms 502a, 502b are deflected away from a central longitudinal axis of the sleeve as a result of distal translation of the sleeve 500 over the struts. The lighter the color, the greater the strain experienced at that location of the arms 502a, 502b. It can be seen in FIG. 5B that the strain, rather than occurring at a single point of the sleeve, is distributed along the arms 502a, 502b. The flexibility of the arms 502a, 502b thus allows them to flex outwardly as they contact the struts to soften the contact edge and associated strain between the sleeve 500 and the struts during use. In some embodiments, softer, more elastic arms 502a, 502b may deform over the struts, increasing contact surface area to more effectively distribute stress during use.

FIG. 5C illustrates a portion of a frame 505 showing the sleeve 500 in use, where the sleeve 500 has been distally translated over struts 512a, 512b to pull together the struts 512a, 512b and the anchors 510a, 510b. As shown in FIG. 5C, as the sleeve 500 is translated distally, the arms 502a, 502b ride along the respective struts 512a, 512b, deforming the distal end of the sleeve 500 in accordance with a shape of the frame. As a result, the stresses are distributed more evenly along arms 502a, 502b, and the potential for fatigue over time is reduced. Although not required, in some embodiments the arms 502a, 502b may be coated on an internal surface with a smooth polymer or other material to further reduce the impact of friction and abrasion of the frame by the arms 502a, 502b.

Referring now to FIGS. 6A-6C, it is recognized that in use an annular implant experiences chronic torsion and other three-dimensional stresses caused by movement of the heart muscle. FIG. 6A illustrates one embodiment of a resilient sleeve 600 including a helical sleeve slot 620 which extends through or partially through sleeve body 610 and is circumferentially disposed about a distal end 607 of sleeve 600. According to one aspect, the helical slot may be used to dampen three-dimensional stresses. In one embodiment, the helical sleeve slot 620 initiates at an entry point 615 of the sleeve 600 and extends proximally at an angle relative to an axis defined by a distal end 607 of the sleeve. The helical sleeve slot 620 may continue about the sleeve 620 for a number of turns, until disposed about an extent 605 of the sleeve 600, essentially transforming the distal end 607 of the sleeve 600 into a helical coil that is expandable in at least three dimensions along the extent 605. Thus, in the embodiments of FIGS. 6A-6C, because the helical slot 620 is disposed about the circumference of the sleeve, the overall length of the helical slot 620, from entry point 615 to terminating cut, may exceed the length of the sleeve 600. In addition, helical slots having similar extents may vary in length depending upon the pitch of the helical cut. In various embodiments of resilient sleeves including helical slots 620, the extent 605 may vary from between 5%-55%, or 50%-75% of a length of the sleeve 600.

In some embodiments the helical slot may extend partially around or fully around the sleeve. In some embodiments, the helical slot may extend around the sleeve for multiple turns. In some embodiments, the helical slot may be continuous or alternatively may be non-continuous (dashed). In some embodiments, the helical slot may cut through an external surface of the sleeve, but not an internal surface of a sleeve bore. In some embodiments, the helical slot may cut through the internal surface of the sleeve bore, but not through the external surface of the sleeve. In some embodiments the helical slot may vary in pitch as it ascends/descends along the sleeve 600.

FIG. 6B illustrates the distal end 607 of the sleeve 600 in more detail. In some embodiments, because a helical slot 620 initiates with an angular cut at initiation point 615 into or through the surface 610 of the sleeve 600, and because the angled cut may undesirably provide a sharp edge to the implant, a dulling feature, such as divot 618, may be provided to minimize contact between sharp edges and annular tissue. Other methods for softening the edge, such as cutting in perpendicularly before starting the helix, or starting the helix by cutting through the surface without creating an edge, etc., could readily be substituted herein by those of skill in the art.

FIG. 6C illustrates a portion of an implant 640 including a frame 633 having a sleeve 600 distally advanced over struts 612a, 612b. As shown in FIG. 6C, the helical slots 620 enable the distal end of the sleeve 600 to conform in shape to the struts 612a, 612b. As a result, the three-dimensional torsion forces are distributed to minimize the potential for fatigue of frame 633.

Figure 7A:
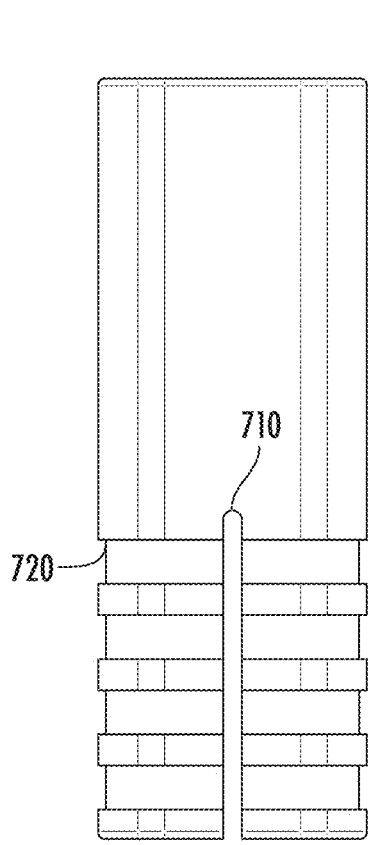
FIGS. 7A and 7B illustrate an embodiment of a resilient sleeve in accordance with the present disclosure.
Figure 7B:
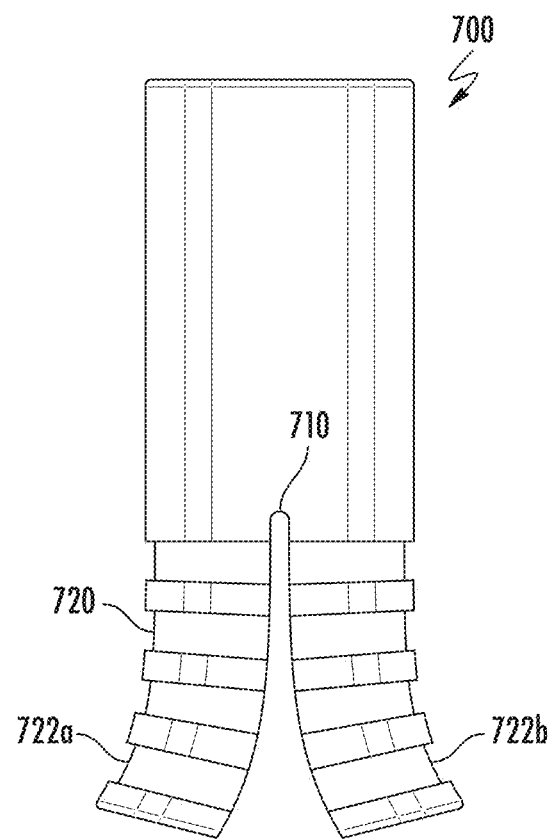

FIGS. 7A and 7B illustrate an alternate embodiment of a sleeve 700 including a combination of resiliency features such as a sleeve slot 710 as well as several cutouts, such as cutout 720. For the purposes of this description, a cutout is a cut through or partially through a surface 710 of the sleeve 700, wherein at least a portion of sleeve material is removed, and/or a thickness of the sleeve is otherwise varied. In FIGS. 7A and 7B, the cutouts are shown to extend circumferentially around the sleeve 700. In some embodiments, the cutouts may extend partially around the sleeve 700, or be provided as individual holes or other form of cutout that are disposed at various locations on various surfaces of the sleeve 700 that may benefit from increased flexibility. Although FIGS. 7A and 7B illustrate cutouts from an external surface of sleeve 700, in other embodiments, cutouts may also or alternatively be disposed upon the internal surface, such as the bore wall.

FIG. 7B is a representative illustration of sleeve 700 in use, for example where the sleeve 700 has been advanced over a proximal apex of a frame such that arms 722a, 722b of the sleeve are spread apart as they ride over the frame. As shown in FIG. 7B, the cutout 720 changes the thickness of the sleeve 700 for the extent of the cutout 720, thereby increasing the flexibility and/or deformability of the sleeve 700 at the cutout 720. While the cutouts 720 are shown of uniform spacing and pattern, it is appreciated that in various embodiments the cutouts may vary in size, width or spacing to compensate for the particular forces experienced by the frame. For example, in some embodiments, cutouts that are more closely spaced may provide sleeve portions of added flexibility, while cutouts that are spaced farther apart may provide more rigidity to the sleeve structure.

Various methods for modifying sleeve resiliency using slots or other cutouts have been described. According to one aspect, sleeve resiliency may be further improved by changing the composition of the sleeve. For example, in various embodiments the resiliency characteristics of a sleeve may be improved by manufacturing the sleeve at least in part using resilient materials having an increased elasticity and ability to more easily deform over the struts to more effectively distribute sleeve forces. Such materials include, but are not limited to, Nitinol, cobalt chrome, stainless steel, titanium, and the like.

Figure 8:
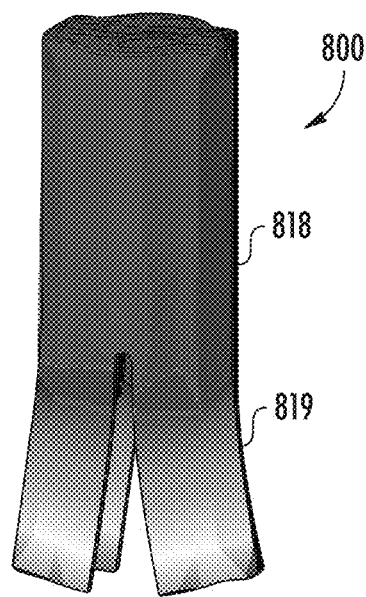
FIG. 8 illustrates an embodiment of a resilient sleeve in accordance with the present disclosure.

In some embodiments, the sleeve may be made of a single material with increased resilience. In other embodiments, the sleeve may be manufactured to include multiple materials that vary in resilience. For example, FIG. 8 is a drawing of a sleeve 800 that has been shaded such that portions of the sleeve manufactured from materials having a lower resilience are darker than those portions of the sleeve having a higher resilience. For example, the portion 818 of the sleeve that supports the drive shaft may have a higher stiffness to facilitate operation of the drive shaft, and a lower stiffness, or increased flexibility to enable the distal end 818 to facilitate deformation of the distal end 819 over struts.

In some embodiments, the sleeve may be formed of graphene, and/or a polymer that may be coated with a solid coating such as graphite and/or a drug eluting coating. The body of the sleeve may comprise a braided coil tube, like a catheter, encompassed in a polymer sheath. Some embodiments may comprise a braid disposed over a coil, the combination encapsulated by a polymer. Alternatively, a braided sheath encapsulating a threaded inner component that is a molded, thermoformed component may be used. Furthermore, a coiled, reinforced sheath that incorporates the threaded inner bore may be used herein.

Figure 9A:
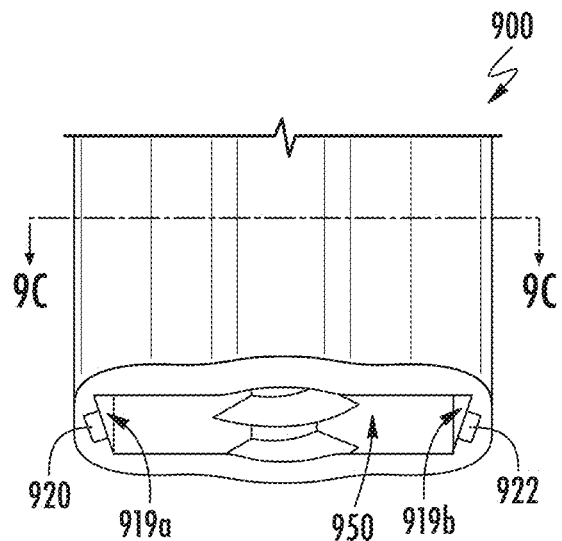
FIGS. 9A and 9B illustrate perspective views and FIG. 9C illustrates a cross-sectional view, along line 9C-9C of FIG. 9A, of an embodiment of a resilient sleeve in accordance with the present disclosure.
Figure 9B:
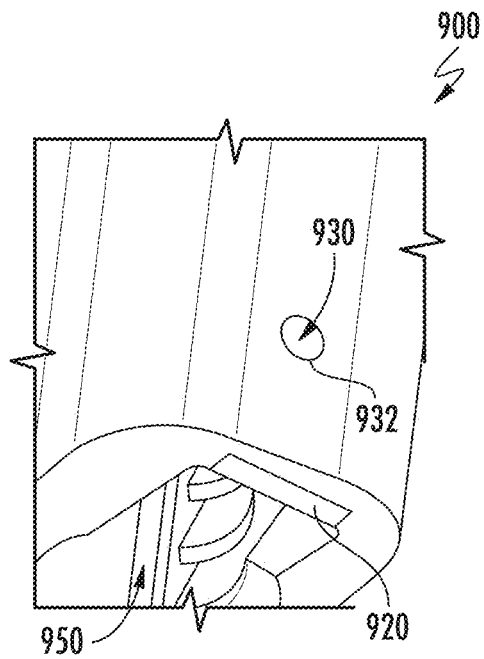
Figure 9C:
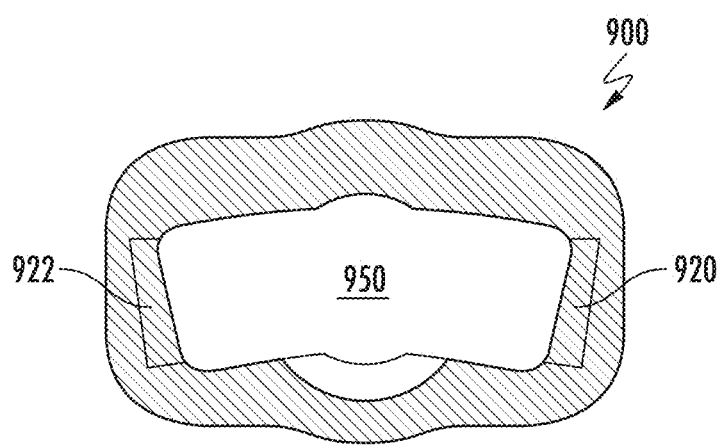

While it has been described above that different sleeves may be manufactured using different materials to form a unitary body, in other embodiments a sleeve may be formed of multiple materials and/or may be adapted to include additional components to reduce stress at the frame. For example, FIGS. 9A-9C illustrate the introduction of bumpers to a resilient sleeve 900. FIG. 9A illustrates a distal portion of one embodiment of a resilient sleeve 900 having a bore 950 extending therethrough. As discussed above, the sleeve 900 may experience stress at lower distal corners as indicated by arrows 919a, 919b from chronic contact with struts during use, and bumpers 920, 922 may be configured to dampen the impact of the chronic contact.

FIG. 9B illustrates a distal end of the sleeve 900 in more detail. Bumper 920 is preferably formed of a material that is softer and/or more resilient than that of sleeve 900. For example, bumper 920 may be made of a softer material such as a polymer that conforms to the strut without leaving particulate to reduce abrasion that may lead to fatigue. In some embodiments the bumper 920 may comprise an internal bore coating that is integral with the sleeve 900. In other embodiments, the bumper 920 may be comprised of a discrete component that may be press fit into the bore 950 of the sleeve 900 during the manufacturing process. For example, each bumper 920 may include a nub or tab 930 that may be press fit into a hole or recess 932 within the bore 950 of the sleeve 900.

FIG. 9C is a cross section taken along line 9C-9C of FIG. 9A. As shown in FIG. 9C, a bumper 920, 922 may be disposed on opposing sides of the bore 950, in particular where the frame (not shown) contacts the internal surface of the bore 950 during use. The size, position and shape of the bumpers 920, 922 may vary in accordance with the particular shape of the frame and the contact points between the frame and the sleeve 900. Although two bumpers are shown, it is appreciated that the number of bumpers is not so limited, and that various combinations of coatings and/or bumpers disposed at contact points within a bore may advantageously reduce frame fatigue to maintain frame integrity during use.

Figure 10:
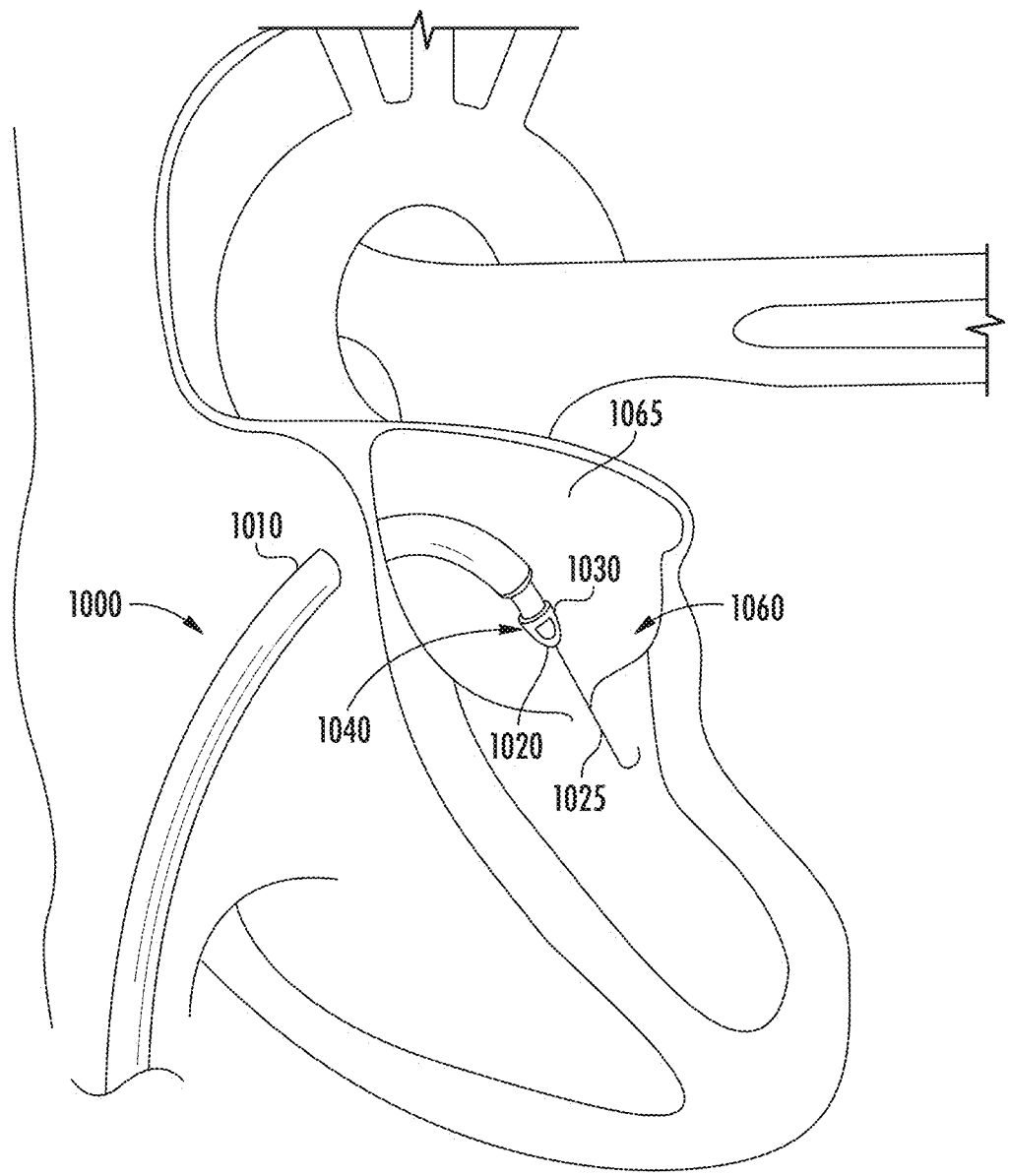
FIG. 10 illustrates an exemplary deployment system, which may be used with embodiments of implants in accordance with the present disclosure.

Accordingly, various embodiments of annular valve implants providing customizable valve shaping with resilient actuator sleeves have been shown and described. Such implants may be part of a valve annulus reshaping system 1000 such as that shown in FIG. 10 which is shown to include a deployment catheter 1010 having a distal tip 1020 comprising a distal sheath 1040 and an extendable guidewire 1025 extending therethrough to guide the deployment catheter 1010 into position proximate to a valve annulus 1060. Deployment catheter 1010 may measure about twenty to thirty centimeters in length for accessing the atrium 1065 and the mitral valve annulus 1060 through the apex of the heart. Deployment catheter 1010 may access the vasculature of the leg, in particular the femoral vein or the iliac vein for transluminal deployment to a cardiac annulus.

An implant 1030 including actuator sleeves having one or more resiliency features such as those disclosed herein may be disposed within the distal sheath 1040 of the deployment catheter during deployment.

Figure 11:
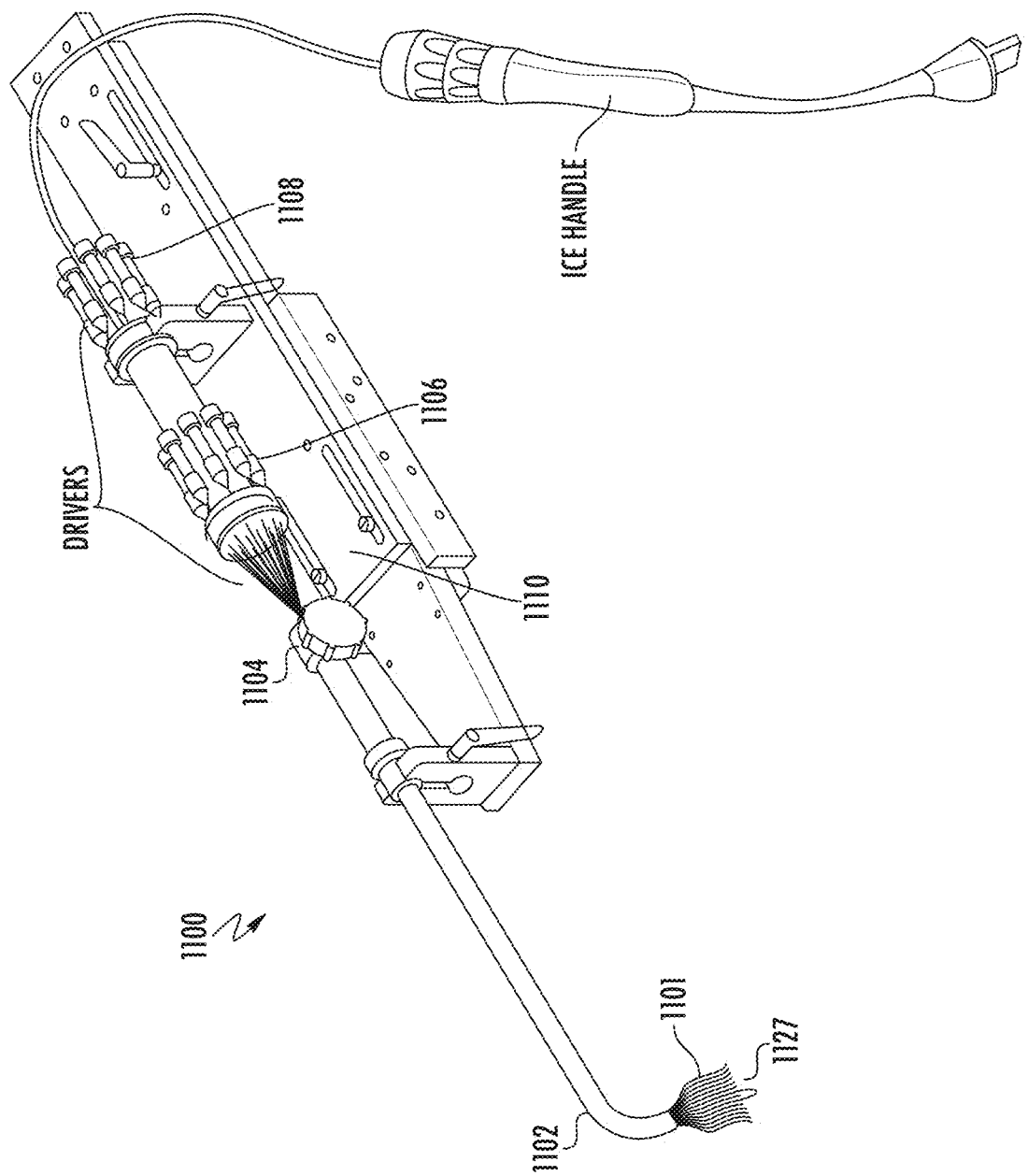
FIG. 11 illustrates additional components of the deployment system of FIG. 10.

FIG. 11 illustrates a deployment system 1100 that may be used to deploy an implant 1101 for annular reshaping as described herein. The deployment system 1100 comprises a steerable sheath 1102, a sheath steering knob 1104, cinch knobs 1106, anchor knobs 1108, the implant 1101, and a visualization probe 1127, supported by a base 1110. The cinch knobs 1106 and anchor knobs 1108 may be spring loaded to maintain tension. Cinch knobs 1106 may be manipulated by an operator to compress an expandable frame, to anchor the frame, and/or to reduce a valve annulus by advancing the resilient actuator sleeves along the struts.

It should be noted that, although the disclosure has focused on the use of actuator sleeves that are rotatably driven over a frame, the principles disclosed herein are not limited to use with rotating actuators. Other actuation sleeves, including sleeves that are pushed or otherwise ratcheted down over frame struts to adjust strut spacing may similarly benefit from the inclusion of resiliency features such as those described herein. For example, the principles disclosed herein may also improve the fatigue tolerance for implants such as those disclosed, for example, in U.S. patent application Ser. No. 14/861,877, entitled "ADJUSTABLE ENDOLUMENAL IMPLANT FOR RESHAPING MITRAL VALVE ANNULUS", and filed on Sep. 22, 2015

(issued on Apr. 11, 2017, as U.S. Pat. No. 9,615,926); as described, for example, in U.S. patent application Ser. No. 15/280,004, entitled "METHODS FOR DELIVERY OF HEART VALVE DEVICES USING INTRAVASCULAR ULTRASOUND IMAGING", and filed on Sep. 29, 2016 (issued on Jul. 2, 2019, as U.S. Pat. No. 10,335,275); as described, for example, in U.S. patent application Ser. No. 15/043,301, entitled "VALVE REPLACEMENT USING ROTATIONAL ANCHORS", and filed on Feb. 12, 2016 (issued on Dec. 26, 2017, as U.S. Pat. No. 9,848,983); as described, for example, in U.S. patent application Ser. No. 15/352,288, entitled "IMPLANTABLE DEVICE AND DELIVERY SYSTEM FOR RESHAPING A HEART VALVE ANNULUS", and filed on Nov. 15, 2016 (issued on Feb. 11, 2020, as U.S. Pat. No. 10,555,813); as described, for example, in U.S. patent application Ser. No. 14/427,909, entitled "MITRAL VALVE INVERSION PROSTHESES", and filed on Mar. 12, 2015 (issued on Apr. 4, 2017, as U.S. Pat. No. 9,610,156), and/or as described, for example, in U.S. patent application Ser. No. 15/893,122, entitled "IMPLANTABLE DEVICE AND DELIVERY SYSTEM FOR RESHAPING A HEART VALVE ANNULUS", and filed on Feb. 9, 2018 (issued on Feb. 4, 2020, as U.S. Pat. No. 10,548,731), the entire disclosure of each of which is incorporated herein by reference for all purposes and forms a part of this specification. Thus, the description of particular features and functionalities herein is not meant to exclude other features and functionalities, such as those described in the references incorporated herein by reference or others within the scope of the development.

Various modifications to the implementations described in this disclosure will be readily apparent to those skilled in the art, and the generic principles defined herein can be applied to other implementations without departing from the spirit or scope of this disclosure. Thus, the disclosure is not intended to be limited to the implementations shown herein but is to be accorded the widest scope consistent with the claims, the principles and the novel features disclosed herein. The word "example" is used exclusively herein to mean "serving as an example, instance, or illustration." Any implementation described herein as an "example" is not necessarily to be construed as preferred or advantageous over other implementations, unless otherwise stated.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features can be described above as acting in certain combinations and even initially claimed as such, one or more features from a claimed combination can in some cases be excised from the combination, and the claimed combination can be directed to a sub-combination or variation of a sub-combination. Similarly, while operations are depicted in the drawings in a particular order, this should not be understood as requiring that such operations be performed in the particular order shown or in sequential order, or that all illustrated operations be performed, to achieve desirable results. Additionally, other implementations are within the scope of the following claims. In some cases, the actions recited in the claims can be performed in a different order and still achieve desirable results.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The devices and/or methods disclosed and claimed herein can be made and executed without undue experimentation in light of the present disclosure. While various embodiments of the devices and methods of this disclosure have been described, it may be apparent to those of skill in the art that variations can be applied to the devices and/or methods and in the steps or in the sequence of steps of the method described herein without departing from the concept, spirit and scope of the disclosure. All such similar substitutes and modifications apparent to those skilled in the art are deemed to be within the spirit, scope and concept of the disclosure as defined by the appended claims.

What is claimed is:

1. An implant comprising:
   a frame having a proximal end, a distal end, and adjacent struts joined at an apex; and
   a sleeve disposed about the apex and having a proximal end towards the frame proximal end and a distal end towards the frame distal end;
   wherein:

the sleeve is configured to apply a force to the frame at one or more contact points;

the sleeve includes a resiliency feature selected to reduce stress resulting from the force at the one or more contact points;

the resiliency feature comprises at least two sleeve slots extending from the distal end of the sleeve towards the proximal end of the sleeve for a slot extent; and the at least two sleeve slots differ from each other by at least one of a different length, a different width, a different extent, or a different pattern.

2. The implant of claim 1, wherein the sleeve is comprised of a sleeve material including one or more of nitinol, stainless steel and cobalt chrome and the sleeve material varies in resistance along a length of the sleeve.

3. The implant of claim 2, wherein the sleeve comprises a sleeve body having a bore extending therethrough, and the sleeve comprises a first material disposed within the bore and a second material disposed at least partially around the bore, the first material and the second material having different elasticities.

4. The implant of claim 3, wherein the first material coats at least a portion of the bore proximate to at least one contact point.

5. The implant of claim 4, wherein the first material comprises a bumper.

6. The implant of claim 1, wherein at least one of the sleeve slots varies in width over the slot extent.

7. The implant of claim 1, wherein a width of at least one of the sleeve slots is greater than half a width of the sleeve.

8. The implant of claim 1, wherein at least one of the sleeve slots extends linearly along the sleeve or helically around the sleeve for the slot extent.

9. The implant of claim 1, wherein at least one of the sleeve slots extends helically around the sleeve for one or more turns.

10. The implant of claim 9, wherein the at least one of the sleeve slots varies in pitch over the one or more turns.

11. The implant of claim 1, comprising a plurality of sleeve slots.

12. The implant of claim 11, wherein at least two of the plurality of sleeve slots are on different sides of the sleeve.

13. The implant of claim 11, wherein at least two of the plurality of sleeve slots are disposed on opposing sides of the sleeve or a common side of the sleeve.

14. The implant of claim 11, wherein at least two of the plurality of sleeve slots comprise one or more or a different slot length, a different slot width, a different extent, or a different slot pattern.

15. An implant delivery system comprising:

a delivery catheter;

a frame having a compressed configuration for advancement through the delivery catheter to a valve annulus and an expanded configuration for placement of the frame proximate the valve annulus for repair, the frame having a proximal end, a distal end, and adjacent struts joined at an apex; and an actuator comprising a sleeve disposed about the apex and configured to be driven over the apex by pushing or rotating the actuator to compress the frame to a cinched configuration in which a force is applied to the adjacent struts to adjust a space between the adjacent struts, the sleeve having a proximal end towards the frame proximal end and a distal end towards the frame distal end;

wherein:

the sleeve includes a resiliency feature configured to reduce the force exerted by the sleeve on the adjacent struts;

the resiliency feature comprises at least two sleeve slots extending from the distal end of the sleeve towards the proximal end of the sleeve for a slot extent; and the at least two sleeve slots differ from each other by at least one of a different length, a different width, a different extent, or a different pattern.

16. The implant delivery system of claim 15, wherein the resiliency feature includes at least one of a sleeve material and a sleeve feature comprising one or more sleeve slots extending vertically or horizontally along one or more sides of the sleeve.

17. The implant delivery system of claim 15, wherein at least one sleeve slot varies in width along its extent.

18. An implant for a valve annulus, the implant comprising:

a frame having a proximal end, a distal end, and adjacent struts joined at an apex; and a sleeve disposed about the apex, the sleeve configured to apply a force to the frame at one or more contact points, the sleeve including a resiliency feature selected to reduce stress resulting from the force at the one or more contact points;

wherein:

the sleeve has a proximal end towards the frame proximal end, a distal end towards the frame distal end, a first pair of opposing surfaces extending between the proximal end and the distal end, and a second pair of opposing surfaces extending between the proximal end and the distal end;

the first pair of opposing surfaces are wider than the second pair of opposing surfaces; and the resiliency feature comprises at least one slot extending from a distal end of at least one of the surfaces of the first pair of opposing surfaces towards the proximal end of the sleeve, and at least one slot extending from a distal end of at least one of the surfaces of the second pair of opposing surfaces towards the proximal end of the sleeve.

19. The implant of claim 18, wherein the resiliency feature includes at least one of a sleeve material and a sleeve feature comprising one or more sleeve slots extending vertically or horizontally along one or more sides of the sleeve.

20. The implant of claim 18, wherein at least one slot in at least one of the surfaces of the first pair of opposing surfaces, and at least one slot in at least one of the surfaces of the second pair of opposing surfaces differ from each other by at least one of a different length, a different width, a different extent, or a different pattern.

* * * * *